US00PP27668P2

(12) United States Plant Patent
Lee

(10) Patent No.: US PP27,668 P2
(45) Date of Patent: Feb. 14, 2017

(54) ***LAGERSTROEMIA* PLANT NAMED 'DELEF'**

(50) Latin Name: *Lagerstroemia indica*
Varietal Denomination: DELEF

(71) Applicant: Robert Edward Lee, Independence, LA (US)

(72) Inventor: Robert Edward Lee, Independence, LA (US)

( * ) Notice: Subject to any disclaimer, the term of this patent is extended or adjusted under 35 U.S.C. 154(b) by 0 days.

(21) Appl. No.: 14/756,876

(22) Filed: Oct. 21, 2015

(51) Int. Cl.
*A01H 5/00* (2006.01)

(52) U.S. Cl.
USPC ..... Plt./252

(58) Field of Classification Search
USPC ..... Plt./252
See application file for complete search history.

*Primary Examiner* — Annette Para
(74) *Attorney, Agent, or Firm* — Cassandra Bright

(57) ABSTRACT

A new and distinct *Lagerstroemia* cultivar named 'DELEF' is disclosed, characterized by distinctive Greyed-Purple foliage and dark pink flowers. Plants maintain distinctive foliage color throughout growing season and show increased tolerance for Cercospora leaf spot (*C. lythracearum*). The new cultivar is a *Lagerstroemia*, suitable for ornamental garden purposes.

2 Drawing Sheets

Figure 1:
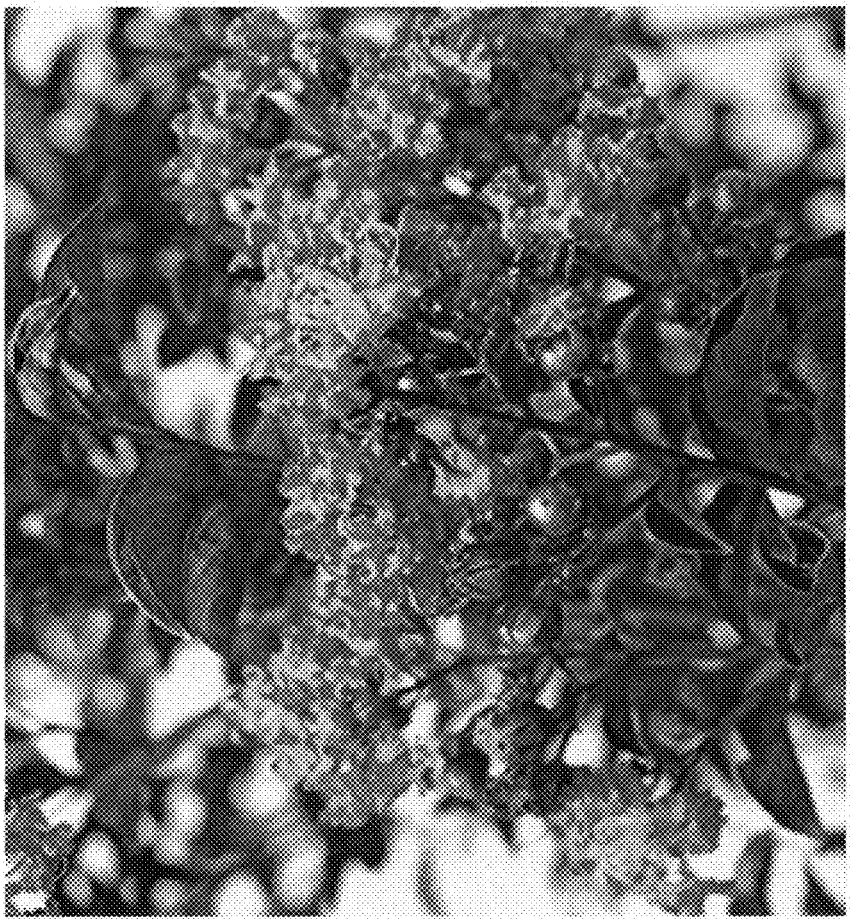

Latin name of the genus and species: *Lagerstroemia indica.*

Variety denomination: 'DELEF'.

BACKGROUND OF THE INVENTION

The new cultivar is a product of a planned breeding program by the inventor, Robert Edward Lee. The inventor's intention was to develop *Lagerstroemia* hybrid plants with dark foliage and resistance to Cercospora leaf spot (*C. lythracaerum*). This new variety, hereinafter referred to as 'DELEF', was discovered as a seedling, resulting from an open pollination of several *Lagerstroemia indica* varieties. Seed was bulk collected from several seed parents, with the actual seed and pollen parents unidentified. The new variety was selected by the inventor during Summer of 2007 at a commercial nursery in Independence, La.

After identifying the new variety as a potentially interesting selection, the inventor first organized propagation of 'DELEF' by vegetative cuttings Fall of 2007 at the same commercial nursery in Independence, La. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'DELEF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DELEF' These characteristics in combination distinguish 'DELEF' as a new and distinct *Lagerstroemia* cultivar:

1. Unique dark red-purple leaf color.
2. Dark foliage color maintained throughout growing season.
3. Deep pink flower color.
4. Increased tolerance for Cercospora leaf spot (*C. lythracearum*).

COMPARISON TO PARENT VARIETY

Parents cannot be identified.

COMMERCIAL COMPARISON

'DELEF' can be compared to the commercial variety *Lagerstroemia* hybrid 'Chocolate Mocha' U.S. Plant Pat. No. 21,540. Plants of the new cultivar 'DELEF' are similar to plants of 'Chocolate Mocha' in most horticultural characteristics, however, plants of the new cultivar 'DELEF' differ in the following:

1. 'DELEF' produces dark pink blooms, this comparator produces light pink blooms.
2. Plants of 'DELEF' produce longer inflorescence than this comparator.

'DELEF' can be compared to the commercial variety *Lagerstroemia* hybrid 'WhitIV', U.S. Plant Pat. No. 11,342. Plants of the new cultivar 'DELEF' are similar to plants of 'WhitIV' in most horticultural characteristics, however, plants of the new cultivar 'DELEF' differ in the following;

1. 'DELEF' has dark pink flowers, 'WhitIV' produces red flowers.
2. Foliage of 'DELEF' is darker than foliage of 'WhitIV'.
3. Dark foliage color of 'DELEF' is maintained throughout the growing season, whereas foliage of 'WhitIV' is dark green, changing to bronze in the Fall.

'DELEF' can be compared to the variety *Lagerstroemia* hybrid 'DELEE', U.S. Plant patent application Ser. No. 14/756,877. Plants of the new cultivar 'DELEF' are similar to plants of 'DELEE' in most horticultural characteristics, however, plants of the new cultivar 'DELEF' differ in the following;

1. 'DELEF' has dark pink flowers, 'DELEE' produces medium pink flowers.
2. Foliage of 'DELEF' is slightly darker Greyed-Purple than foliage of 'DELEE'.
3. Plants of 'DELEF' are somewhat more open, producing less lateral branches than plants of 'DELEE'.

BRIEF DESCRIPTION OF THE PHOTOGRAPHS

The accompanying photograph in FIG. 1 illustrates in full color a close up of typical flowers of the new variety.

Figure 2:
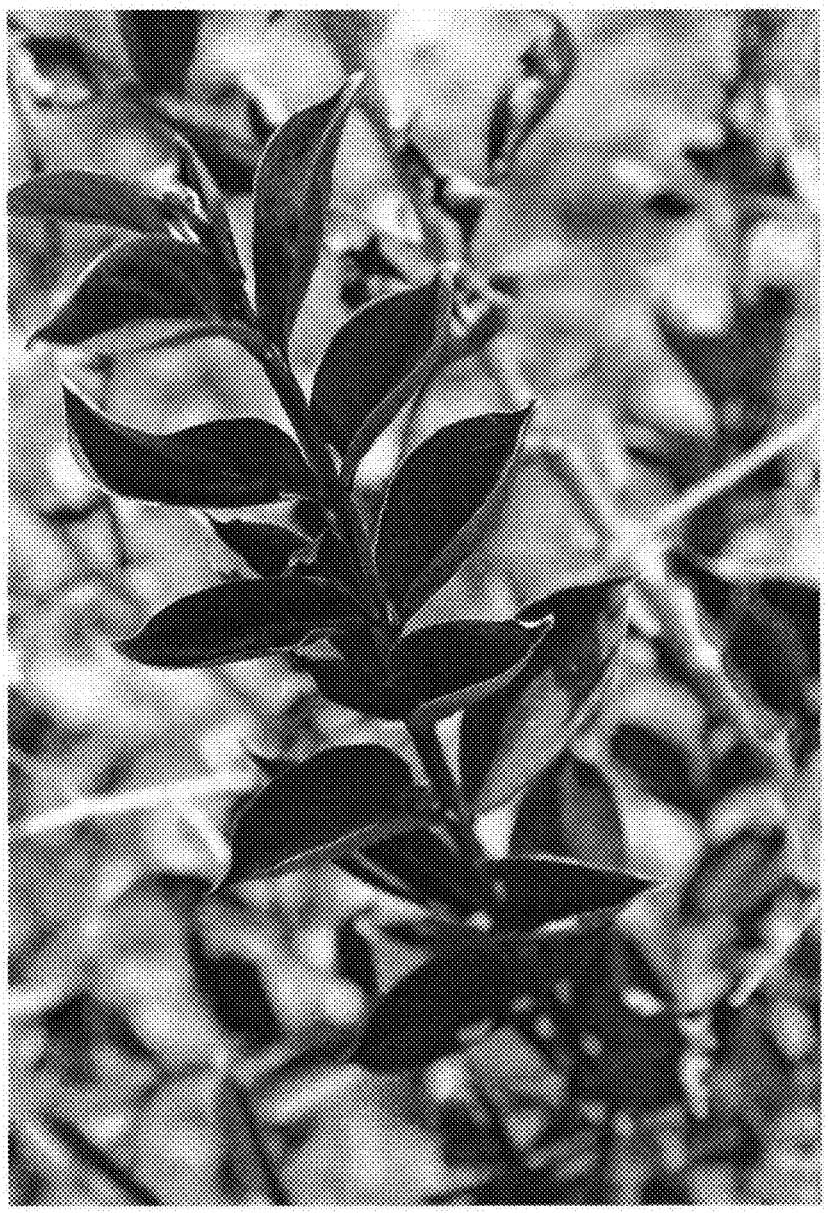

FIG. 2 illustrates dark foliage and stems of the variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DELEF' plants grown outdoors in Loxley, Ala. Plants are approximately 2 years old, in a 3 gallon nursery container. Measurements and numerical values represent averages of typical plant types.

DETAILED BOTANICAL DESCRIPTION

PROPAGATION

Typical propagation: Terminal cuttings.

Time to initiate roots: About 21 days at approximately 30° C.

Root description: Fine, woody, dense. Colored near Grey-Brown 199A.

PLANT

Growth habit: Upright, multi-stemmed small tree or shrub.

Age of plant described: Approximately 2 years.

Height: Approximately 80 cm.

Plant spread: Approximately 70 cm.

Trunk: Average 3 to 5 main stems, which develop into multi-trunked tree or shrub.

- *Diameter*.—Approximately 3.9 cm, after 2 to 3 years.
- *Color*.—Near RHS Brown N200B and near RHS Brown N200C.
- *Texture*.—Slightly scaly.
- *Lenticels*.—Not Present.

Branching characteristics: Branches occurring at approximately 45° from trunk.

- *Length of primary lateral branches*.—Approximately 65 cm.
- *Diameter of lateral branches*.—Approximately 2.0 cm.
- *Approximate quantity of lateral branches*.—3 lateral branches per main stem.

Young shoots:

- *Coloration*.—Near RHS Red-Purple 59A.
- *Texture*.—Ridged.
- *Pubescence*.—Scant to none.
- *Lenticels*.—Not Present.

FOLIAGE

Leaf:

- *Arrangement*.—Alternate. Foliage occurring in close alternate pairs. Pairs more widely spaced apart. Internode space between pairs average range 1.5 to 2.5 cm, internode space between paired leaves approximately 0.3 cm.
- *Quantity*.—Approximately 28 per main branch.
- *Average length*.—Approximately 4.0 cm.
- *Average width*.—Approximately 2.5 cm.
- *Shape of blade*.—Elliptic.
- *Apex*.—Slightly cuspidate.
- *Base*.—Cuneate.
- *Margin*.—Entire, even/smooth throughout.
- *Aspect*.—Upwardly cupped.
- *Texture of top surface*.—Glabrous.
- *Texture of bottom surface*.—Glabrous.
- *Color*.—Young foliage upper side: Near RHS Greyed-Purple N186A, slight tinge RHS Greyed-Green N189A. Young foliage under side: Near RHS Grey-Brown N199A heavily flushed Greyed-Purple N186A. Mature foliage upper side: Near RHS Greyed-Purple N186A slight tinge near RHS Greyed-Green N189A. Mature foliage under side: Near RHS Yellow-Green 147A, heavily flushed Greyed-Purple N186C.
- *Venation*.—Type: Pinnate. Venation color upper-side: Near RHS Greyed-Purple 187A. Venation color under side: Near RHS Greyed-Purple 187B.
- *Petiole*.—Length: Approximately 0.2 cm. Width: Approximately 0.1 cm. Color: Near RHS Red-Purple 59A. Texture: Glabrous.

FLOWER

Natural flowering season: Summer through Fall.

Inflorescence type and habit: Panicle.

Quantity of flowers per inflorescence: Approximately 150 to 250 flowers.

Inflorescence size:

- *Diameter*.—Approximately 17.0 cm.
- *Height*.—Approximately 20.0 cm.

Individual flowers:

- *Size*.—Diameter: Approximately 3.5 cm. Length: Approximately 1.2 cm.

Petals:

- *Petal quantity*.—6 to 12.
- *Size*.—Length: 1.2 cm. Width: 1.3 cm.
- *Margin*.—Highly lobate, highly undulate.
- *Apex*.—Obtuse.
- *Base*.—Cordate.
- *Texture*.—Glabrous.

Color: Petals.

- *When opening*.—Inner surface: Near RHS Red-Purple N74A. Outer surface: Near RHS Red-Purple N74A.
- *Fully opened*.—Inner surface: Between RHS Red-Purple N74B and Red-Purple 71A. Outer surface: Near RHS Red-Purple 67A.

*Color changes when aging*.—Inner surface: Near RHS Red-Purple N74B. Outer surface: Near RHS Purple 75A.

Bud:

*Shape*.—Spherical.

*Length*.—Approximately 0.8 cm.

*Diameter*.—Approximately 0.7 cm.

*Color*.—Near RHS Red-Purple 59B.

Peduncle:

*Length*.—Average 10.0 cm.

*Diameter*.—0.3 cm.

*Color*.—Near RHS Greyed-Purple 187A.

*Texture*.—Glabrous.

*Aspect*.—Straight. Angle of attachment, approximately 25° angle. from stem.

Pedicel:

*Length*.—Average 0.5 cm.

*Diameter*.—0.1 cm.

*Color*.—Near RHS Greyed-Purple N186B.

*Texture*.—Glabrous.

Fragrance: Faint pleasant floral fragrance.

REPRODUCTIVE ORGANS

Stamens:

*Number*.—Approximately 25.

*Filament length*.—Approximately 0.9 cm.

*Filament color*.—Near RHS White 155C.

Anthers:

*Length*.—Less than 0.1 cm, close to 0.5 mm.

*Shape*.—Rounded.

*Color*.—Near RHS Yellow 9A.

*Pollen*.—Quantity: Abundant. Color: Near RHS Yellow 10B.

Pistil:

*Number*.—5.

*Length*.—Approximately 1.5 cm.

*Style*.—Length: Approximately 1.5 cm. Color: Near RHS Greyed-Red 179B.

*Stigma*.—Shape: Rounded. Color: Near RHS Green 138A. Ovary: Color: Near RHS Yellow 10C. Size: Approximately 0.2 cm. Shape: Spherical.

OTHER CHARACTERISTICS

Seeds and fruits: Seed pods/fruit shrivel without forming.

Disease/pest resistance: Increased tolerance for Cercospora leaf spot (*C. lythracearum*).

Temperature tolerance: USDA Zones 7, 8, 9.

What is claimed is:

1. A new and distinct cultivar of *Lagerstroemia* plant named 'DELEF' as herein illustrated and described.

* * * * *